US007901774B2

United States Patent
Höland et al.

(10) Patent No.: US 7,901,774 B2
(45) Date of Patent: Mar. 8, 2011

(54) COATED DENTAL POWDERS

(75) Inventors: Wolfram Höland, Schaan (LI);
Christian Ritzberger, Nenzing (AT);
Norbert Moszner, Triesen (LI); Harald Kerschbaumer, Klaus (AT); Volker Rheinberger, Vaduz (LI); Ricardo Dellagiacoma, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 549 days.

(21) Appl. No.: 11/883,114

(22) PCT Filed: Jan. 19, 2006

(86) PCT No.: PCT/EP2006/050389
§ 371 (c)(1),
(2), (4) Date: Aug. 13, 2007

(87) PCT Pub. No.: WO2006/079619
PCT Pub. Date: Aug. 3, 2006

(65) Prior Publication Data
US 2008/0138768 A1    Jun. 12, 2008

(30) Foreign Application Priority Data
Jan. 27, 2005  (DE) .................. 10 2005 003 755

(51) Int. Cl.
*B32B 5/22*    (2006.01)
*B32B 17/00*   (2006.01)

(52) U.S. Cl. ......... 428/406; 428/404; 428/407; 428/212; 428/214; 428/220

(58) Field of Classification Search .............. 106/35; 427/214; 428/403, 404, 405, 406, 408, 407; 501/5, 6, 7, 8, 9
See application file for complete search history.

(56) References Cited

U.S. PATENT DOCUMENTS

| 4,412,015 A | 10/1983 | Lustgarten et al. |
| 5,122,418 A | 6/1992 | Nakane et al. |
| 5,367,002 A | 11/1994 | Huang et al. |
| 5,380,530 A * | 1/1995 | Hill .............................. 424/440 |
| 5,698,019 A * | 12/1997 | Frank et al. ...................... 106/35 |
| 5,922,785 A * | 7/1999 | Waller et al. ................... 523/116 |
| 6,623,856 B1 * | 9/2003 | Kodas et al. .................. 428/402 |
| 2004/0134230 A1 | 7/2004 | Kodas et al. |
| 2004/0224087 A1 | 11/2004 | Weimer et al. |

FOREIGN PATENT DOCUMENTS

DE      2 126 419       5/1971

(Continued)

OTHER PUBLICATIONS

Translation of DE 19508586 to Rentsch et al.*
Database WPI, Section CH, Week 199506, Derwent Publications Ltd, London, GB, XP002377395 & JP 06 321515 A (Osaka Cement KK) Nov. 22, 1994.

(Continued)

*Primary Examiner* — Timothy H Meeks
*Assistant Examiner* — Collette Ripple
(74) *Attorney, Agent, or Firm* — Lucas & Mercanti, LLP; Klaus P. Stoffel

(57) ABSTRACT

The present invention relates to an inorganic dental powder, coated with at least one layer comprising inorganic and/or organic substances or consisting thereof, and to a process for its preparation.

13 Claims, 1 Drawing Sheet

FOREIGN PATENT DOCUMENTS

| | | |
|---|---|---|
| DE | 31 15 725 | 5/1982 |
| DE | 30 34 374 | 8/1982 |
| DE | 195 08 596 | 9/1996 |
| DE | 197 41 286 | 4/1998 |
| EP | 1 101 484 | 5/2001 |
| EP | 1 250 895 | 10/2002 |
| GB | 2 386 121 | 9/2003 |
| JP | 5899406 A * | 6/1983 |
| WO | 98/51419 | 11/1998 |

OTHER PUBLICATIONS

Database WPI, Section CH, Week 198329, Derwent Publications Ltd, London, GB, XP002377396 & JP 58 099406 A (Tokuyama Soda KK) Jun. 13, 1983.

Schmidt, H.; Journal of Non-Crystalline Solids 178, pp. 302-312, 1994.

Tossatti et al; Langmuir, 18, pp. 3537-3548, 2002.

* cited by examiner

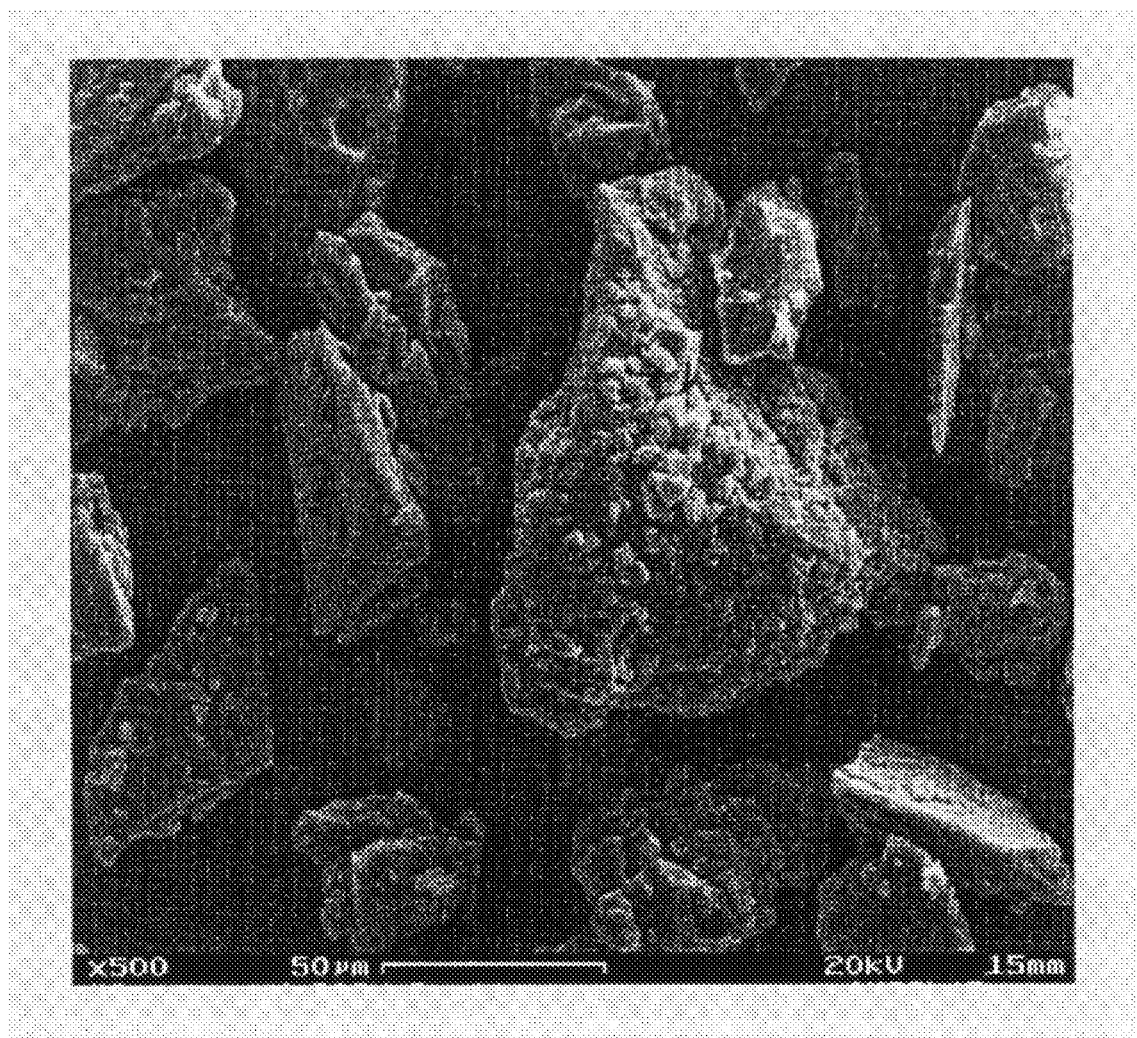

COATED DENTAL POWDERS

The present invention relates to a novel dental powder, and to a process for its preparation.

BACKGROUND OF THE INVENTION

Coatings of glasses, glass ceramics or ceramics with organic materials are known according to the prior art. These coatings are designated as thick or thin layers. The thin layers have thicknesses of nanometer dimension to micrometer dimension. The proportion of substance of these organic coating components in comparison to the substrate material ranges from 0.2 mass % to about 5 mass %. Typical examples of such thin coatings are the simple application to glass fibers, the application of sol-gel layers to glasses (Schmidt, H., J. Non-Cryst. Sol. 178, 1994, 302) or the application of molding aids to ceramic powders for the production of high-strength ceramics, e.g. $ZrO_2$.

Thin coatings of monolithic bodies consisting of metal or ceramic are presented by Tossatti et al. (Langmuir, 18, 2002, 3537). These coatings are biocompatible organic components which have, for example, a particular blood compatibility and have been applied to Ti metal or $TiO_2$. Coating of powders is not mentioned.

On the other hand, it is known of dental powders which [lacuna] for the coating of substrates, e.g. of metal structures (e.g. of a dental crown, or of a multiple-membered bridge) or the coating of metal-free restorations, e.g. of glass ceramic (dental crown or three-membered bridge) for the optimal processing of the powders that mixing fluids have to be used in order to produce highly viscous or viscous slips. These mixing fluids allow the dental technician to produce a slip having optimal consistency from the dental powder. Thus the dental technician is able to apply the material to the suprastructure (e.g. crown, or bridge) using a brush and ideally to model the shape of the crown or bridge using this application process. The excess liquid is aspirated or removed using a hot air dryer. Subsequently, the next layer of slip is applied. The mixing fluids are aqueous media containing small amounts of organic and inorganic components.

After this coating process of the substrate with slip and initial removal of the liquid, the subsequent heat treatment is carried out from room temperature up to the termination of the sintering process, which is typically between 700° C. and 1000° C. Despite the use of mixing fluids, at various times situations occur where the dental powder does not adhere optimally to the substrate during the heat treatment, such that an optimal jointing process between dental powder and the substrate is not achieved in the finished product. This is visible in that, preferably in the approximal region of a crown or in the interdental region between individual crown segments of a multiple-membered bridge, a tearing or a lifting of the dental ceramic from the substrate is observed. If a situation of this type occurs, the dental technician has to apply an additional layer of slip in order to fill this resulting gap.

On the other hand, it is known of pulverulent dental ceramics, dental glass ceramics or dental glasses that during the shrinkage operation in the process of tightly sintering, uncontrolled reactions can occur, which alter the desired geometry ("distortion of a molded part").

In DE 195 08 586 A1, the use of particles as a filler in filling composites which consist of an $SiO_2$ core and are coated with another oxide is described. The focal point in the specification is the production of composites having specific X-ray opaque properties and an adjustable translucency. The possible subsequent coating of these "two-layer" $SiO_2$ particles with an organic layer serves for the improved incorporation of these fillers into the organic matrix of the filling composite.

DE 197 41 286 A1 describes spherical particles which consist of an $SiO_2$ core and/or further oxides and have a specific order of magnitude. In addition, these are coated with a polymerizable binder, this coating making possible covalent bonding of these particles to the polymer matrix and in this way guaranteeing a high strength of the organic/inorganic compound system in the composite.

US 2004/0224087 A1 describes the preparation and use of mixed oxide particles which consist of a number of layers of different oxides as fillers in dental composites, where one of the outer layers of the particles is essentially constructed of $SiO_2$. The oxides of the core of the particles are constructed from various metals and have a higher refractive index than $SiO_2$ alone.

US 2004/0134230 A1 also describes the preparation of fillers for composites. These glass powders have specific chemical properties and morphologies. In one case, these particles are also coated with organic materials, where the object of this coating is the better binding of these particles to the resin matrix.

EP 1 101 484 A2 describes fillers for dental composites. The fillers are not suitable for veneers of dental structures.

The particles described in DE 30 34 374 A1 are incorporated into dental composites as fillers. This coating consists of curable (polymerizable) plastics, preferably those from the organic matrix of the dental material. These coated particles are not employable as a glassy or glass ceramic veneer for dental restoration.

U.S. Pat. No. 4,412,015 relates to fillers for dental materials primarily based on barium fluorosilicate glasses or zeolites. The coating of the particles with the curable organic compounds serves exclusively for the increased strength of the compound system between the inorganic particles and the polymer matrix.

In WO 98/51419, a particle core of a sintered ceramic is described which is surrounded by a second metal compound. This coating is capable of entering into a permanent bond with other metals. As a whole, these particles are to be assigned to the sintered metallurgical products and are not comparable with the glassy or glass ceramic particles (dental powders).

EP 1 250 895 A2 relates to a process for the production of dental ceramic molded parts using electrophoretic deposition of oxide ceramic particles on a dental technology model. The slip described is deposited electrophoretically on a model and the oxide ceramic green article thus obtained after a drying process is tightly sintered at temperatures between about 1100° C. and approximately 1700° C. Afterward, veneering is carried out in a manner known from the prior art.

U.S. Pat. No. 5,122,418 describes the preparation of a powder for cosmetic applications, certain properties of course also being predominant in this case.

In summary, it is to be observed that not one coating of the dental powder which has good and advantageous processing properties in the processing and heat treatment is described in the prior art mentioned.

SUMMARY AND DESCRIPTION OF THE INVENTION

The object of the invention consists in applying a coating, preferably a nanocoating, to a dental powder, whereby, when using a liquid, preferably water, a slip of the type results which is readily processable and an optimal jointing and adhesion to the substrate is achieved without a joint gap occurring. Furthermore, it is the aim to achieve optimal shrinkage reactions of dental powders (ceramics, glass ceramics, glasses) without substrates.

This object is achieved by an inorganic dental powder which is coated with at least one layer comprising inorganic or organic substances or consisting of these substances.

It was surprisingly found that an inorganic powder coated with organic components made possible a high adhesion of the inorganic powder to the substrate and inorganic components, such as, for example, $ZnCl_2$, make possible an optimal processing and stability of the aqueous slips. The additionally surprising effect consisted in the fact that both mechanisms acting oppositely per se could be realized by the coating on a pulverulent dental material.

For characterization of the coated dental powder, the zeta potential was determined. It was seen here that the zeta potential for various dental powders consisting of glasses, glass ceramics and/or ceramics was in the range from +100 to −150, preferably in the range from +50 to −80. Measurement was carried out here against a background electrolyte, which preferably is the same inorganic component as in the solution for the coating of the dental powder.

The powders employed according to the invention are preferably crystalline, glass ceramic, glassy or amorphous. Suitable dental powders are glasses, or glass ceramics consisting of silicate, aluminate, borate or phosphate substance systems. Further examples of these glasses or glass ceramics are special systems based on an aluminosilicate, aluminophosphosilicate, or aluminoborosilicate. Such substance systems contain, for example: $SiO_2$—$Al_2O_3$—$Na_2O$—$K_2O$; or $SiO_2$—$Al_2O_3$—$Na_2O$—$K_2O$—$CaO$—$P_2O_5$; or $SiO_2$—$Li_2O$.

The glass ceramics can contain main crystal phases, such as, for example, leucite, or apatite, or leucite and apatite.

The sintered ceramics can contain silicate materials, e.g. silicate glasses and feldspar crystals, or aluminum oxide or zirconium oxide as the main constituent.

The particle size of the used dental powders of the glass ceramics, glass-containing sintered ceramics or glass-containing composites with and without crystal phases can preferably be between 5 and 100 µm, preferably between 5 and 50 µm (measured as the mean particle size $D_{50}$). For dental sintered ceramics, these are in the range between 50 nm and about 2 µm.

The layer thickness of the applied organic or inorganic substances is 0.5 nm to approximately 1 µm, preferably between 0.5 and 200 nm.

For the coating of dental powders (glasses, glass ceramics or ceramics) with organic components, custom polymers are in particular suitable, which on account of their structure allow a specific interaction with a solid body surface of the dental powder and thus lead to corresponding property changes as a result of the modification or coating of the powder surface. Suitable polymers are preferably water-soluble compounds which, for the interaction with the solid body surface, carry capable functional groups, where the interaction can take place by means of dipole-dipole, ion-dipole and ion-ion interactions, and by means of hydrogen bonds and complexation. The polymer modification of the particles then leads to mechanisms of the type known in polymer-solid dispersions, such as steric stabilization, bridging effect or separation. Typically, water-soluble polymers are especially those which are of linear construction and contain a large number of hydrophilic groups. Here, the hydrophilic groups can be subdivided into nonionic {e.g. —OH, —O—, —$NH_2$, —NHR, —$NR_2$, —SH, —CO—NH—, —O—CO—NH—, —NH—CO—$NH_2$, —COOH, —P(O)(OH)$_2$}, anionic (—COO$^-$, —$PO_3^{2-}$, —$SO_3^{2-}$) cationic ($NH_3^+$, —$NR_3^+$) and zwitterionic groups (—$NR_2^+$—O$^-$, —$NR_2^+$—$(CH_2)_n$—$SO_3^-$) and hybrid macromolecules. The water-soluble polymers include synthetic polymers of the type such as polyvinyl alcohol, polyethylenimine, poly-acrylamide, polyethylene oxide, polyethylene glycol, homo- and copolymers of (meth)acrylic acid, maleic acid, vinylsulfonic acid and vinylphosphonic acid, polyvinylpyrrolidone and biopolymers of the type such as starch, alginates, gelatin or cellulose ethers, such as, for example, carboxymethylcellulose.

Beside the homopolymers, copolymers having a custom structure, which allow an optimal interaction with the solid body surface, are also suitable here. The copolymer composition can be adjusted to the reactivity of the powder surface, such that a strong interaction of the monomer units of the macromolecules with the reactive centers of the powders is possible. For example, more acidic monomer units promote a more intense ionic interaction with mainly basic surfaces or monomer units which contain heteroatoms (N, O) make possible hydrogen bridges with superficial OH groups of the solid powders. Moreover, chelating monomer units, such as, for example, units having diketone or salicylate groups, can be selectively incorporated which allow a coordination-chemical interaction, especially with transition metal atoms, such as, for example, Ti or Zr. Finally, the thickness of the coating of the particle surface can also be varied by means of the architecture of the copolymers. Thus it is known that, for example, custom block and comb polymers are particularly suitable for the surface modification of solid body surfaces. Possible controllable structural parameters are, inter alia, the nature of the monomer units of the polymer segments, the segment length and the segment distribution.

The coating of the dental powders can preferably be carried out by means of two methods:
1. By coating of the powders with molecules according to the principle of self-organization of particles on powder surfaces during the reaction in aqueous media.
2. By specific coating processes, preferably by fluidized bed treatment of the powders.

For the First Process:

Organic and/or inorganic components are applied in one or more reaction steps. In the multistage process, it is proceeded, for example, in such a way that a certain proportion of substance of an organic component is incorporated into distilled water and the dental powder is subsequently added thereto and is homogenized for a time of about 1 minute to 1 hour by, for example, stirring. By means of self-organization, the coating of the dental powder with the organic component takes place. Afterward, the liquid is separated from the powder (e.g. filtering) and the powder is dried at 80 to 200° C. for 10 minutes to 15 hours. Possible formation of lumps occurring slightly is destroyed by shaking or gentle crushing or sieving. In the second reaction step, a second aqueous liquid is treated/doped with inorganic components and the powder already coated with the organic component is added thereto, homogenized, dried and prepared according to the first reaction step.

The second process comprises carrying out a coating with organic and inorganic components, e.g. in a fluidized bed unit, from Glatt, Switzerland.

As a starting material for the subsequent exemplary embodiments, a leucite-apatite glass ceramic having a mean particle size $D_{50}$ of about 30 µm was used.

For the comparison of the individual dental powders, three different types are usefully conceivable:

1. uncoated dental powder,
2. dental powder coated with organic (PEG 10,000) and inorganic substances ($ZnCl_2$), coating by means of fluidized bed technology according to exemplary embodiment 2,
3. dental powder coated with organic (PEG 10,000) and inorganic substances ($ZnCl_2$) in aqueous solution, coating according to exemplary embodiment 1.

1. Uncoated Dental Powder

In the uncoated dental powder, isolated particles of all orders of magnitude can be discerned in the SEM image, optionally individual small particles lie insignificantly on other, larger particles.

2. Fluidized Bed Technology 2.1 The layer thickness of the coating of the dental powder with the abovementioned organic and inorganic substances is quite obviously below 1 μm, very probably even below 100 nm.

2.2 A very large fraction of the particles of the fine-grain spectrum (particles smaller than 25% of the $D_{50}$, in the example case mentioned that is less than 5 μm) are found on the surface of large particles. The fixing of the particles is relatively strong and cannot be broken up and the small particles removed from the surface even by direct irradiation with a 20 kV electron beam.

2.3 Neither within the dental powder nor on the surface do the small particles agglomerate together to give relatively large particle collections (formation of aggregates), as is known, for example, in the preparation of $ZrO_2$ or $Al_2O_3$ ceramics.

3. Liquid Technology

In this technology too, the statements made under 2. apply, however the number of small particles to the large ones is somewhat smaller, which is certainly to be attributed to the different processes.

From the SEM investigations, the following conclusions can now be drawn in comparison to the dental technological preparation of a glass ceramic layer on a dental substrate by heat treatment:

It is known that the shrinkage process of the dental powder during the heat treatment to about 900° C. is influenced by various parameters. Surprisingly, it was found that by means of the specific packing density, that by the larger particles, which are adhered to small ones, has a particular advantage on the shrinkage. The shrinkage process in conjunction with the release of volatile constituents (liquid of the slip, liberation of the enclosed air etc.) is markedly lower with the dental powder according to the invention than with uncoated dental powder. The result of the experiments shows that the physicochemical reactions of shrinkage, the release of volatile gaseous constituents and the activation of the particles in the "low-temperature range" (not only below the sintering temperature, but even also below the transformation range of the glass matrix of the leucite-apatite glass ceramic used) are of particular importance and as a result of the dental powder according to the invention no distortion of the desired geometry or lifting of the substrate occurs up to the sintering temperature.

During the sintering process, the small particles of the fine-grain spectrum of the dental powder are of particular importance. These small particles have, in comparison to the larger ones, a high sintering activity and initiate the sintering process. At the same time, owing to their more rapidly occurring liquidity, these make possible the production of a compact and low-pore dental restoration (cf. FIGURE).

BRIEF DESCRIPTION OF THE DRAWING:

The single FIGURE shows a compact and low-pore dental restoration.

EXAMPLES

EXEMPLARY EMBODIMENT

Self-Organisation of Monolayers of Organic and Inorganic Substances on Inorganic Powders in Aqueous Solutions Coating of a Leucite-Apatite Glass Ceramic with PEG and $ZnCl_2$:

For the coating of 60 g of glass ceramic powder of mean particle size $D_{50}$ of 32 μm, 26.58 g of PEG solution (content of PEG: 1.0 mass %) were needed.

These amounts of powder and liquid were determined in a preliminary experiment in which for the coating of a three-membered dental metal bridge with 5.53 g of powder and 2.45 g of mixing fluid were performed. The 60 g of glass ceramic were weighed into a beaker, the 26.58 g of solution were added and the mixture was made up to 100 g with distilled water. Following this, it was stirred for 20 minutes. Subsequently, the separation of the liquid from the powder was carried out by filtering through a glass sinter suction funnel and a suction bottle at low vacuum. The filter cake was skimmed off and dried at 80° C. and a residence time of 12 h. A few resulting small lumps formed are pulverized by means of pressure.

The zeta potential of this dental powder coated with organic molecules was subsequently measured with the ESA 8000 apparatus, Matec appl. Sci., Northborough, Mass., USA. $ZnCl_2$ solution was used as a background electrolyte. In the present exemplary embodiment, a suspension having an 8% by volume solids content was prepared. This corresponds to 50.8 g of powder+230 ml of solution, a zinc chloride solution being used as the background electrolyte. The addition of 1M $ZnCl_2$ solution was carried out with stirring. A nanocoating with inorganic molecules on the surface of the dental powder already coated with organic molecules took place. Both processes of nanocoating were carried out according to the principles of self-organization. As the last process step, the powder coating was filtered, dried and prepared for use.

Result of the Zeta Potential Measurement:

1. Powder: Leucite-Apatite Glass Ceramic Coated with PEG-6000
   a) corresponds to: powder with PEG coated before $ZnCl_2$ coating
   b) corresponds to: powder with PEG coated after $ZnCl_2$ coating
   a) PRG-6000 2 mass %: −73.8 mv ζ potential
   b) +2.3 ml of $ZnCl_2$ 1M: +25.7 mV ζ potential
2. Powder: leucite-apatite glass ceramic coated with PEG-10000
   a) PEG-10 000 1.0 mass %: −64.6 mV ζ potential
   b) +1.7 ml of $ZnCl_2$ 1 M: −20.6 mV ζ potential These dental powders having a nanocoating were applied in the dental technological experiment to metal structures which were coated with an opaquer. A procedure was used here in which a ready-to-use slip was produced from the powders by addition of distilled water. These slips were applied to four-membered metal bridges coated with opaquers. The heat treatment was carried out in a P 100 oven, Ivoclar Vivadent AG, under the following parameters:

heating rate: 60 K/min from room temperature to 890° C.
vacuum from 400° C. to 890° C.
residence time at 890° C.: 1 min After cooling the dental restorations, it was seen that the wetting of the applied nanocoating glass ceramic with the structure in the cervical region of the dental bridge was good for the variants using PEG-6000, and using PEG-10 000. The sample type using PEG-10 000, however, showed the best reaction behavior with respect to the total jointing compound system and the shrinkage of the dental ceramic.

Likewise, sample platelets were produced by this process and their optical parameters were determined. In comparison to an uncoated/uncoated sample, no discoloration at all by carbon residues was seen. In the sintering process, the organic constituents have been burned out without a residue to 890° C.

Exemplary embodiment 2 shows details of the burning-out process.

EXEMPLARY EMBODIMENT

Fluidized Bed Coating

As a starting material, 1 kg of the same leucite-apatite glass ceramic powder as in example 1 was used.

This powder was coated with a solution of the content of 1.0 mass % of PEG 1000. For coating, the GLATT fluidized bed granulator GPC G1.1 (manufacturer Glatt, Switzerland) is used.

The powder is filled into the funnel of the Glatt unit and the tube of the conveyor pump is immersed in the PEG solution.

The parameters had to be adjusted, but are adjusted during the coating process. Care was to be taken that the amount of liquid and feed air temperature were adjusted such that the powder did not form lumps.

Experimental Parameters:

| | |
|---|---|
| Feed air temp.: | 35-40° C. |
| Spray pressure: | 1 bar |
| Pump position: | 30-35% |
| Amount sprayed: | about 14.2 ml/min |
| Amount of air: | 80-120 m³/h |
| Time of coating: | 70.5 min |
| Drying time: | until a product temperature of 24° C. is reached |

In the result of this experiment, the coated glass ceramic powder was investigated in a heat experiment by means of thermogravimetry. The assessment of this experiment showed that in the range from about 350 to 400° C. a mass loss of about 1.0 mass % occurred, which corresponds to the content of PEG-1000, because the PEG decomposes in this temperature range.

The invention claimed is:

1. An inorganic dental powder consisting of glasses or glass ceramics based on an aluminosilicate, aluminophosphosilicate or aluminoborosilicate, coated with one layer comprising inorganic substances and one layer comprising organic substances, in a total layer thickness of 0.5 nm-1 μm, for use as an aqueous slip, wherein the organic substances are water-soluble polymers, wherein the coating contains $ZnCl_2$ or $AlCl_3$ as inorganic substances.

2. The inorganic dental powder as claimed in claim 1, wherein the total layer thickness is 0.5-200 nm.

3. The dental powder as claimed in claim 1, wherein the average particle size is 50 nm to 100 μm.

4. The dental powder as claimed in claim 1, wherein the average particle size is 5-50 μm.

5. The dental powder as claimed in claim 1, which contains one or more crystal phases.

6. The dental powder as claimed in claim 1, which as crystal phases contains leucite or fluoroapatite or mixtures thereof.

7. The dental powder as claimed in claim 1, wherein the zeta potential of a slip produced by addition of water to the powder is +100 to −150 mV.

8. The dental powder as claimed in claim 1, wherein the polymers are compounds having hydrophilic groups or hybrid macromolecules.

9. The dental powder as claimed in claim 8, wherein the hydrophilic groups are nonionic, anionic, cationic or zwitterionic groups.

10. The dental powder as claimed in claim 1, which contains synthetic polymers or biopolymers.

11. The dental powder as claimed in claim 10, wherein the synthetic polymers are polyvinyl alcohol, polyethylenimine, polyethylene oxide, polyethylene glycol, homo- and copolymers of (meth)acrylic acid, maleic acid, vinylsulfonic acid and vinylphosphonic acid, polyvinyl-pyrrolidone and biopolymeric starch, alginates, gelatin or cellulose ethers.

12. The dental powder as claimed in claim 10, wherein the organic polymers are block and comb polymers or homo- and copolymers having chelating monomer units.

13. The dental powder as claimed in claim 7, wherein the zeta potential of a slip produced by addition of water to the powder is +50 to −80 mV.

* * * * *